US012594145B2

(12) United States Patent (10) Patent No.: US 12,594,145 B2

Chang (45) Date of Patent: Apr. 7, 2026

(54) ORTHODONTIC APPLIANCE WITH ORTHOPEDIC FUNCTION

(71) Applicant: TNS CO., LTD., Seoul (KR)

(72) Inventor: Wongun Chang, Seoul (KR)

(73) Assignee: TNS CO., LTD., Seoul (KR)

( * ) Notice: Subject to any disclaimer, the term of this patent is extended or adjusted under 35 U.S.C. 154(b) by 463 days.

(21) Appl. No.: 18/018,231

(22) PCT Filed: Aug. 4, 2021

(86) PCT No.: PCT/KR2021/010216

§ 371 (c)(1),
(2) Date: Jan. 26, 2023

(87) PCT Pub. No.: WO2022/030994

PCT Pub. Date: Feb. 10, 2022

(65) Prior Publication Data

US 2023/0263598 A1 Aug. 24, 2023

(30) Foreign Application Priority Data

Aug. 5, 2020 (KR) ........................ 10-2020-0097719

(51) Int. Cl.
*A61C 7/08* (2006.01)
*A61B 17/66* (2006.01)
(Continued)

(52) U.S. Cl.
CPC .................. *A61C 7/08* (2013.01); *A61C 7/36* (2013.01); *A61B 17/663* (2013.01); *A61C 7/10* (2013.01)

(58) Field of Classification Search
CPC ....................................................... A61C 7/36
See application file for complete search history.

(56) References Cited

U.S. PATENT DOCUMENTS 11,529,256 B2 * 12/2022 Wiele ........................ A61C 7/36
2003/0190576 A1 * 10/2003 Phan ........................ A61C 7/00
433/19

(Continued)

FOREIGN PATENT DOCUMENTS

CN 110974455 A * 4/2020 ............... A61C 7/08
JP 2017-532112 A 11/2017
(Continued)

OTHER PUBLICATIONS

CN 110974455 A (Shen Gang; Shanghai Smartee Denti Tech Co Ltd) (Shen Gang et al.) Dental instrument, tooth correction system, and designing method and preparation method for dental instrument, Apr. 10, 2020 [retrieved on Oct. 2, 2025]. Translation retrieved from: Espacenet (Year: 2020).*

(Continued)

*Primary Examiner* — Eric J Rosen
*Assistant Examiner* — Courtney N Huynh
(74) *Attorney, Agent, or Firm* — Stein IP LLC

(57) ABSTRACT

The present invention relates to an orthodontic appliance with an orthopedic function. The orthodontic appliance includes an upper teeth aligner mounted on user's upper teeth to correct arrangement of the user's upper teeth, a lower teeth aligner mounted on user's lower teeth to correct arrangement of the user's lower teeth, and occlusal force conversion units respectively provided on the upper teeth aligner and the lower teeth aligner, and configured to interact with each other in a state in which the upper and lower teeth aligners are in contact, so as to cause the relative position of a mandible with respect to a maxilla to move to a normal position. The orthodontic appliance is freely attached to and detached from the user's teeth like conventional clear orthodontic appliances so as to be easily used, and thus simul- (Continued)

taneously corrects teeth arrangement and performs orthopedic treatment.

7 Claims, 9 Drawing Sheets

(51) Int. Cl.
A61C 7/10 (2006.01)
A61C 7/36 (2006.01)

(56) References Cited

U.S. PATENT DOCUMENTS

| | | | | |
|---|---|---|---|---|
| 2007/0283967 | A1 | 12/2007 | Bailey | ............................ 128/848 |
| 2015/0238284 | A1* | 8/2015 | Wu | ......................... A61C 7/002 |
| | | | | 703/1 |
| 2017/0035533 | A1 | 2/2017 | Ross | ......................... A61C 7/36 |
| 2017/0273819 | A1* | 9/2017 | Shim | ......................... A61C 7/36 |

FOREIGN PATENT DOCUMENTS

| | | | |
|---|---|---|---|
| KR | 10-2004-0111414 | A | 12/2004 |
| KR | 10-2013-0123111 | A | 11/2013 |
| KR | 10-2202863 | B1 | 1/2021 |

OTHER PUBLICATIONS

International Search Report mailed Nov. 11, 2021, issued to corresponding International Application No. PCT/KR2021/010216.

* cited by examiner

ORTHODONTIC APPLIANCE WITH ORTHOPEDIC FUNCTION

CROSS-REFERENCE TO RELATED APPLICATIONS

This application is a national stage of International Application No. PCT/KR2021/010216, filed Aug. 4, 2021, which claims the benefit of Korean Application No. 10-2020-0097719, filed Aug. 5, 2020, in the Korean Intellectual Property Office, the disclosures of which are incorporated herein by reference.

TECHNICAL FIELD

The present invention relates to an orthodontic appliance worn on teeth, and more particularly, an orthodontic appliance with an orthopedic function which may perform orthopedic treatment alone or may perform both orthodontic treatment and orthopedic treatment at the same time.

BACKGROUND ART

Irregular teeth, malocclusion, facial asymmetry, lantern jaw, or like is mainly caused by improper growth of teeth and jaws due to developmental abnormality of the teeth or jawbones, bad habits affecting the teeth, or heredity.

These various abnormal conditions somewhat negatively affect an individual's first impression, and cause discomfort in daily life, i.e., in chewing at the time of eating foods. This is the reason why there is a continuing interest in tooth correction or maxillary and mandibular orthopedics.

The principle of orthodontics uses the characteristics of a tooth that, when force is applied to the tooth, is moved by the applied force. There are various orthodontic methods and, there among, a method of fixing brackets to teeth and interconnecting the brackets by wires is used as one orthodontic method. Since the brackets and the wires are formed of metal, this orthodontic method is disadvantageous in that the brackets and the wires are readily visible and are uncomfortable to manage.

A method using a clear orthodontic appliance is used as another orthodontic method. In the method using the clear orthodontic appliance, a plurality of clear teeth aligners, to which the step-by-step arrangements of patient teeth changed from the state of the teeth before orthodontic treatment to the state of the teeth after orthodontic treatment are applied, is manufactured, and is sequentially worn on the patient teeth so as to correct teeth arrangement. The clear orthodontic appliance is not visible from the outside, is freely attached to and detached from the teeth as needed, and is thus widely used for adults.

As is well known, the clear orthodontic appliance is manufactured using dental CAD software. That is, each of the movement paths of patient teeth from the positions of the teeth before orthodontic treatment to the positions of the teeth after orthodontic treatment is divided into sections by stages, a database is created using these divided sections, and teeth aligners in respective stages are designed and manufactured based on the database.

Further, when a facial skeletal structure is abnormal, an adult may undergo a surgical operation, or a growing child may be induced to be grown so as to have a normal skeletal structure through orthopedic treatment configured to perform growth induction and inhibition. Such orthopedic treatment is performed using a removable appliance, and the conventional removable appliance has a complicated structure, causes a strong sense of foreign matter, and precludes the possibility of movement of individual teeth.

Therefore, an apparatus having both an orthodontic function and an orthopedic function, which is simple and is easy to use, is required.

DISCLOSURE

Technical Problem

Therefore, the present invention has been made in view of the above problems, and it is an object of the present invention to provide an orthodontic appliance with an orthopedic function, which may be freely attached to and detached from user's teeth like conventional clear orthodontic appliances, and may thus simultaneously correct teeth arrangement and perform orthopedic treatment.

Technical Solution

In accordance with an aspect of the present invention, the above and other objects can be accomplished by the provision of an orthodontic appliance with an orthopedic function including an upper teeth aligner mounted on user's upper teeth to correct arrangement of the user's upper teeth, a lower teeth aligner mounted on user's lower teeth to correct arrangement of the user's lower teeth, and occlusal force conversion units respectively provided on the upper teeth aligner and the lower teeth aligner, and configured to interact with each other in a state in which the upper and lower teeth aligners are in contact, so as to cause a relative position of a mandible with respect to a maxilla to move to a normal position.

In accordance with another aspect of the present invention, there is provided an orthodontic appliance with an orthopedic function including an upper teeth aligner mounted on user's upper teeth to correct arrangement of the user's upper teeth, a lower teeth aligner mounted on user's lower teeth to correct arrangement of the user's lower teeth, and upper covers located on an outer surface of the upper teeth aligner, and configured to isolate gums from muscles configured to surround the gums and thus to block pressure of the muscles applied to the gums so as to cause growth of a maxillary arch.

Further, the orthodontic appliance may further include lower covers located on an outer surface of the lower teeth aligner, and configured to isolate gums from muscles configured to the gums and thus to block the pressure of the muscles applied to the gums so as to cause growth of a mandibular arch.

Further, the upper covers may include an upper anterior teeth cover fixed to a front surface of the upper teeth aligner so as to isolate the gums from lip muscles.

Moreover, the upper covers may include upper posterior teeth covers fixed to both side parts of the upper teeth aligner so as to isolate the gums from cheek muscles.

Further, the lower covers may include a lower anterior teeth cover fixed to a front surface of the lower teeth aligner so as to isolate the gums from lip muscles.

In addition, the lower covers may include lower posterior teeth covers fixed to both side parts of the lower teeth aligner so as to isolate the gums from cheek muscles.

Further, the orthodontic appliance may further include occlusal force conversion units respectively provided on the upper teeth aligner and the lower teeth aligner, and configured to interact with each other in a state in which the upper and lower teeth aligners are in contact, so as to cause a relative position of a mandible with respect to a maxilla to move within a normal position range.

Moreover, the occlusal force conversion units may include upper orthodontic blocks located on some parts of a bottom surface of the upper teeth aligner and configured to protrude downwards, each upper orthodontic block including a pressing inclined plane part, and lower orthodontic blocks located on some parts of an upper surface of the lower teeth aligner and configured to protrude upwards, each lower orthodontic block including a pushed inclined plane part pushed by a pressure applied by the pressing inclined plane part, and the pressing inclined plane part may be lowered while sliding along the pushed inclined plane part to apply the pressure to the pushed inclined plane part at a time of occlusion.

Further, each upper orthodontic block may further include a contact plan part configured to come into contact with the upper surface of the lower teeth aligner, in the state in which the upper and lower teeth aligners are in contact, and each lower orthodontic block may further include a contact plan part configured to come into contact with the bottom surface of the upper teeth aligner, in the state in which the upper teeth aligner and the lower teeth aligner are in contact.

Further, a protrusion configured to extend horizontally from the pressing inclined plane part of each upper orthodontic block may be formed on the pressing inclined plane part, and a locking groove configured to receive the protrusion so as to support the protrusion in the state in which the upper and lower teeth aligners are in contact may be formed in the pushed inclined surface part of each lower orthodontic block.

Moreover, a protrusion configured to extend horizontally from the pushed inclined plane part of each lower orthodontic block may be formed on the pushed inclined plane part, and a locking groove configured to receive the protrusion in the state in which the upper and lower teeth aligners are in contact may be formed on the pressed inclined surface part of each upper orthodontic block.

Further, locking grooves configured to prevent relative lateral movement of the upper and lower orthodontic blocks in the state in which the upper and lower teeth aligners are in contact may be formed in the upper and lower orthodontic blocks.

Advantageous Effects

The orthodontic appliance having the above-described configuration according to the present invention may be freely attached to and detached from user's teeth like conventional clear orthodontic appliances so as to be easy to use, may simultaneously perform both orthodontics of upper and lower teeth and orthopedic treatment, and may achieve normal growth of upper and mandibles together with expansion of a maxillary arch.

Further, the orthodontic appliance according to the present may induce orthopedic treatment and correct eruption of permanent teeth, and may actively induce movement of individual teeth, in the case of a growing child.

MODE FOR INVENTION

Hereinafter, one embodiment of the present invention will be described in more detail with reference to the accompanying drawings.

An orthodontic appliance with an orthopedic function according to the present invention may not only correct user's teeth arrangement but also may balance an abnormal maxilla or mandible, i.e., have the orthopedic function.

The orthodontic appliance includes an upper teeth aligner mounted on user's upper teeth to correct arrangement of the user's upper teeth, a lower teeth aligner mounted on user's lower teeth to correct arrangement of the user's lower teeth, and occlusal force conversion units respectively provided on the upper teeth aligner and the lower teeth aligner, and configured to interact with each other in a state in which the upper and lower teeth aligners are in contact, so as to cause the relative position of a mandible with respect to a maxilla to move to a normal position.

Alternatively, the orthodontic appliance may has a basic configuration including an upper teeth aligner mounted on user's upper teeth to correct arrangement of the user's upper teeth, a lower teeth aligner mounted on user's lower teeth to correct arrangement of the user's lower teeth, and upper covers located on the outer surface of the upper teeth aligner, and configured to isolate gums from muscles surrounding the gums and thus to block pressure of the muscles applied to the gums so as to cause growth of a maxillary arch.

Figure 1:
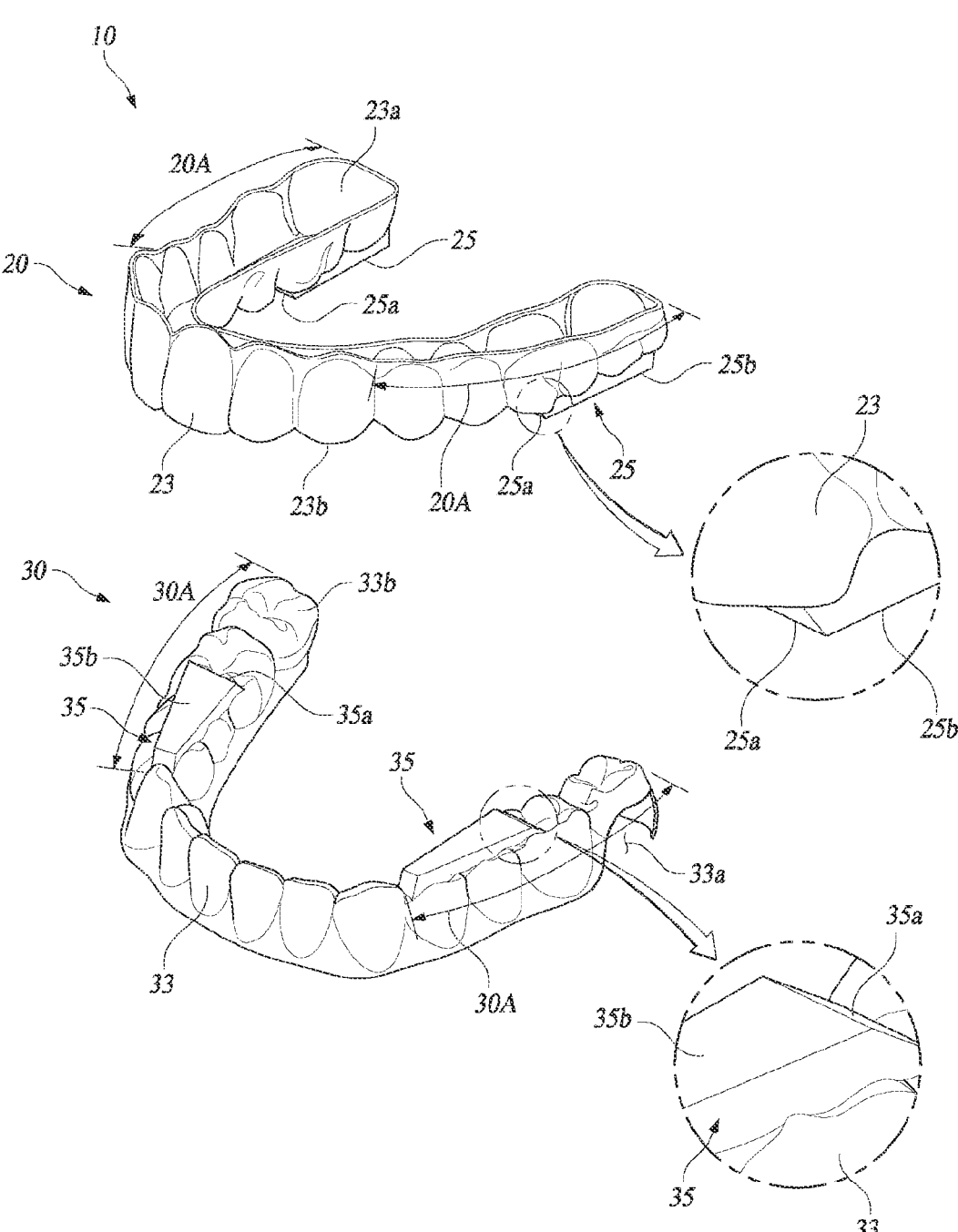
FIG. 1 is a perspective view for illustrating the structure of an orthodontic appliance with an orthopedic function according to one embodiment of the present invention.
Figure 2:
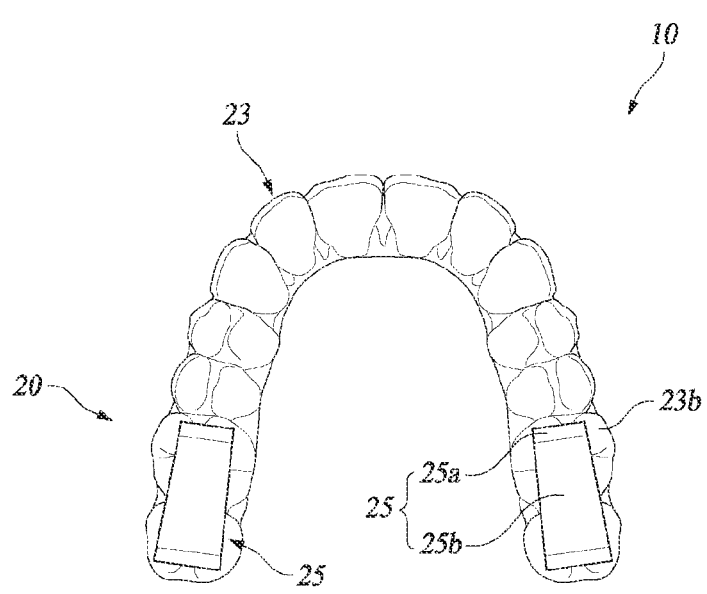
FIG. 2 is a view showing an upper teeth mounting unit and a lower teeth mounting unit shown in FIG. 1.
Figure 2:
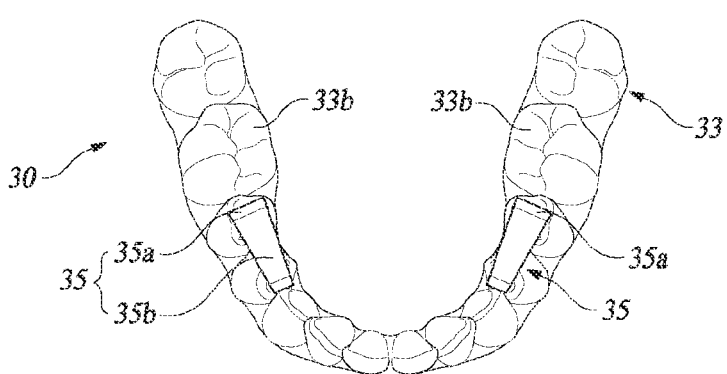
Figure 3:
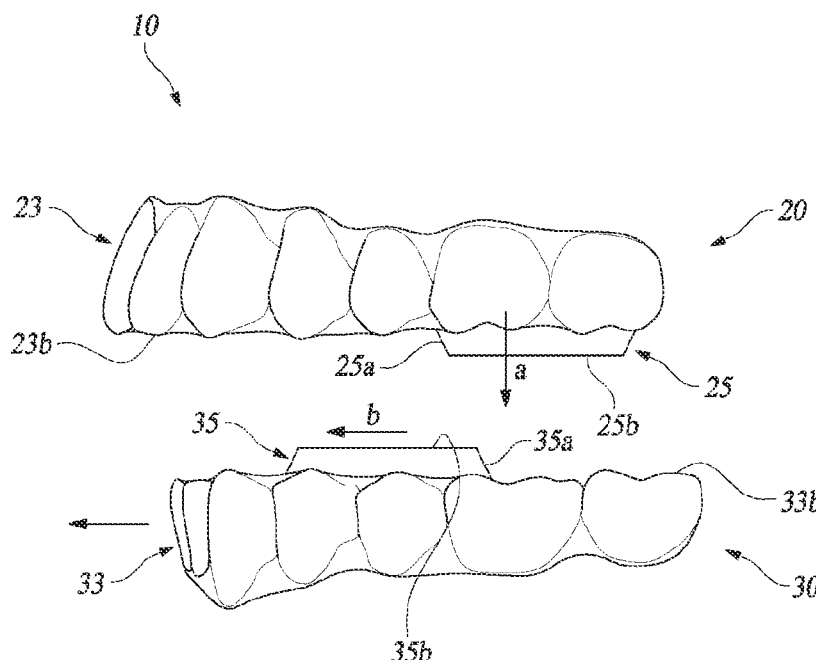
FIG. 3 is a side view for illustrating an orthopedic principle using the orthodontic appliance of FIG. 1.

FIG. 1 is a perspective view for illustrating the structure of an orthodontic appliance 10 with a function of moving a mandible forwards and downwards according to one embodiment of the present invention, and FIG. 2 is a view showing an upper teeth mounting unit and a lower teeth mounting unit shown in FIG. 1. Further, FIG. 3 is a side view for illustrating an orthopedic principle using the orthodontic appliance of FIG. 1.

As shown in these figures, the orthodontic appliance with the orthopedic function according to this embodiment includes an upper teeth mounting unit 20 and a lower teeth mounting unit 30. The upper teeth mounting unit 20 is worn on the user's upper teeth, and the lower teeth mounting unit 30 is worn on the user's lower teeth. The upper teeth mounting unit 20 and the lower teeth mounting unit 30 are formed of the same material as general clear teeth aligners, and are transparent.

The upper teeth mounting unit 20 includes an upper teeth aligner 23 and upper orthodontic blocks 25. The upper teeth aligner 23 and the upper orthodontic blocks 25 are manufactured by vacuum forming or through a 3D printer, and are integrated with each other. Further, the lower teeth mounting unit 30 includes a lower teeth aligner 33 and lower orthodontic blocks 35. The lower teeth aligner 33 and the lower orthodontic blocks 35 of the lower teeth mounting unit 30 are manufactured by vacuum forming or through the 3D printer, in the same manner as in the upper teeth mounting unit 20.

The upper orthodontic blocks 25 and the lower orthodontic blocks 35 are the occlusal force conversion units which cause the relative position of the user's mandible with respect to the user's maxilla to move to the normal position, and a detailed description thereof will be given below.

First, the upper teeth aligner 23 is mounted on the user's upper teeth to correct the arrangement of the user's upper teeth, and has an upper teeth receiving groove 23a into which the user's upper teeth are inserted. As is well known, upper teeth include anterior teeth located in front, canine teeth located behind the anterior teeth, premolar teeth located behind the canine teeth, and molar teeth located behind the premolar teeth. Posterior teeth receiving parts 20A which receive the premolar teeth and the molar teeth are provided at both side parts of the upper teeth aligner 23.

The lower teeth aligner 33 is mounted on the user's lower teeth to correct the arrangement of the user's lower teeth, and has a lower teeth receiving groove 33a into which the user's lower teeth are inserted. In the same manner as the upper teeth, lower teeth include anterior teeth, canine teeth, premolar teeth, and molar teeth. Posterior teeth receiving parts 30A which receive the premolar teeth and the molar teeth are provided at both side parts of the lower teeth aligner 33.

The occlusal force conversion units are respectively provided on the upper teeth aligner 23 and the lower teeth aligner 33, and interact with each other in the state in which the upper and lower teeth aligners are in contact, so as to cause the relative position of the mandible with respect to the maxilla to move to the normal position. For example, the occlusal force conversion units cause the mandible to move forwards, and thereby, balance the upper and mandibles so as to provide airway dilation and breathing improvement effects.

The occlusal force conversion units include the upper orthodontic blocks 25 provided on the bottom surfaces of the posterior teeth receiving parts 20A of the upper teeth aligner 23, and the lower orthodontic blocks 35 provided on the upper surfaces of the posterior teeth receiving parts 30A of the lower teeth aligner 33.

The upper orthodontic blocks 25 are protrusions which protrude downwards from the bottom surface of the upper teeth aligner 23, and each of the upper orthodontic blocks 25 has a contact plane part 25b, which is generally flat, and a pressing inclined plane part 25a. The contact plane part 25b comes into contact with an upper surface 33b of the lower teeth aligner 33 (in the state in which the upper teeth aligner 23 and the lower teeth aligner 33 are in contact). The upper orthodontic blocks 25 are located under the user's upper molar teeth.

Further, the pressing inclined plane part 25a is bent at an obtuse angle from the contact plane part 25b, and slides downwards in the state in which the pressing inclined plane part 25a comes into contact with a pushed inclined plane part 35a of the lower orthodontic block 35, when the upper teeth aligner 23 is lowered in the vertical direction, as shown in FIG. 3. As the pressing inclined plane part 25a is lowered in the direction of an arrow a, the pushed inclined plane part 35a is moved in the direction of an arrow b.

Consequently, the upper orthodontic block 25 presses the lower orthodontic block 35 in the direction of the arrow b, and thus moves the mandible forwards. That is to say, orthopedic treatment for a user having a poor mandible is performed. The angle of the pressing inclined part 25a with respect to a vertical line may be 30 degrees to 50 degrees.

The lower orthodontic blocks 35 are protrusions which protrude upwards from some parts of the upper surface 33b of the lower teeth aligner 33, and each of the lower orthodontic blocks 35 has a contact plane part 35b and the pushed inclined plane part 35a. The contact plane part 35b comes into contact with a bottom surface 23b of the upper teeth aligner 23 in the state in which the upper teeth aligner 23 and the lower teeth aligner 33 are in contact. Further, the pushed inclined plane part 35a is a plane which is bent from the contact plane part 35b, and is pushed by a pressure applied by the pressing inclined plane part 25a. The lower orthodontic blocks 35 may be located on some of the user's lower premolar and molar teeth.

The orthodontic appliance 10 having the above configuration may allow the user's maxilla and mandible to maintain proper positions in the engaged state of the user's teeth through the upper orthodontic blocks 25 and the lower orthodontic blocks 35 provided on the upper teeth aligner 23 and the lower teeth aligner 33, thereby being capable of causing the mandible at an abnormal position to move to the centric relation position or inducing or inhibiting jaw growth.

Figure 4:
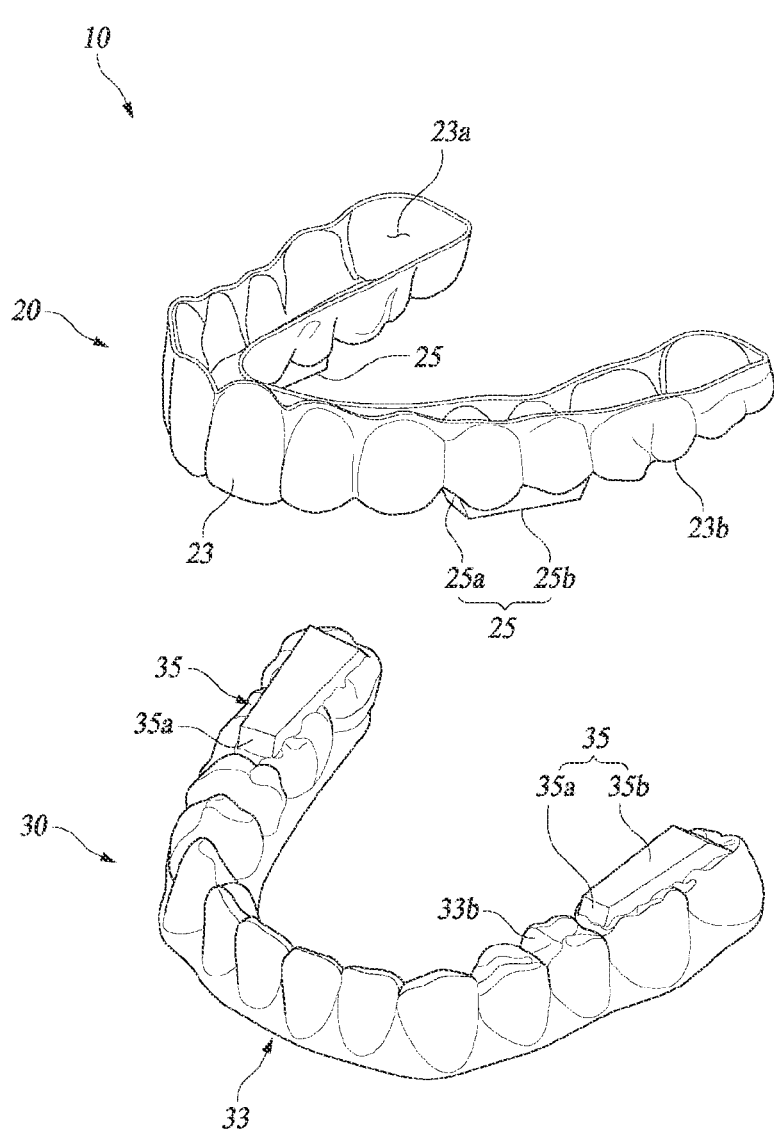
FIG. 4 is a perspective view showing a modified example of the orthodontic appliance according to one embodiment of the present invention.
Figure 5:
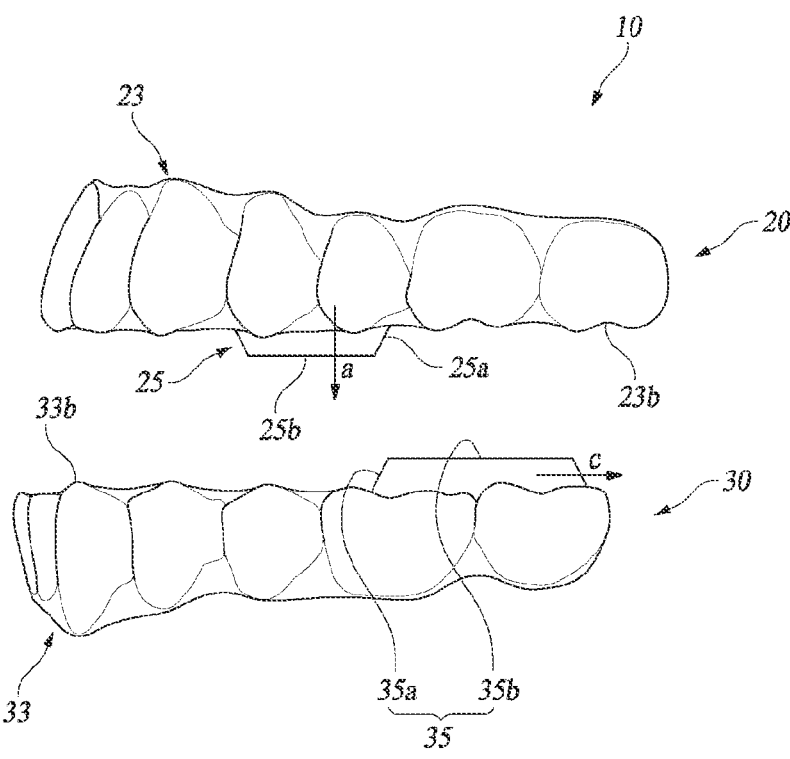
FIG. 5 is a side view of the orthodontic appliance shown in FIG. 4.

FIG. 4 is a perspective view showing a modified example of the orthodontic appliance 10 according to one embodiment of the present invention, and FIG. 5 is a side view of the orthodontic appliance shown in FIG. 4.

Hereinafter, the same reference numerals indicate the same members having the same functions.

As shown in these figures, the positions of the upper orthodontic blocks 25 and the lower orthodontic blocks 35 are opposite to the positions shown in FIG. 1. That is, the upper orthodontic blocks 25 are located under some of the user's upper premolar and molar teeth wearing the upper teeth aligner 23, and the lower orthodontic blocks 35 are located on the user's lower molar teeth wearing the lower teeth aligner 33.

The pressing inclined plane parts 25a of the upper orthodontic blocks 25 and the pushed inclined plane parts 35a of the lower orthodontic blocks 35 are located above and below, and, when a user closes his/her mouth, i.e., when the upper orthodontic block 25 is lowered in the direction of an arrow a, the upper orthodontic block 25 presses the pushed inclined part 35a in the direction of an arrow c.

The orthodontic appliance 10 having this structure may not only correct the arrangement of the user's upper teeth and lower teeth but also may cause the user's mandible to move rearwards so as to perform orthopedic treatment of a patient having a lantern jaw.

Figure 6:
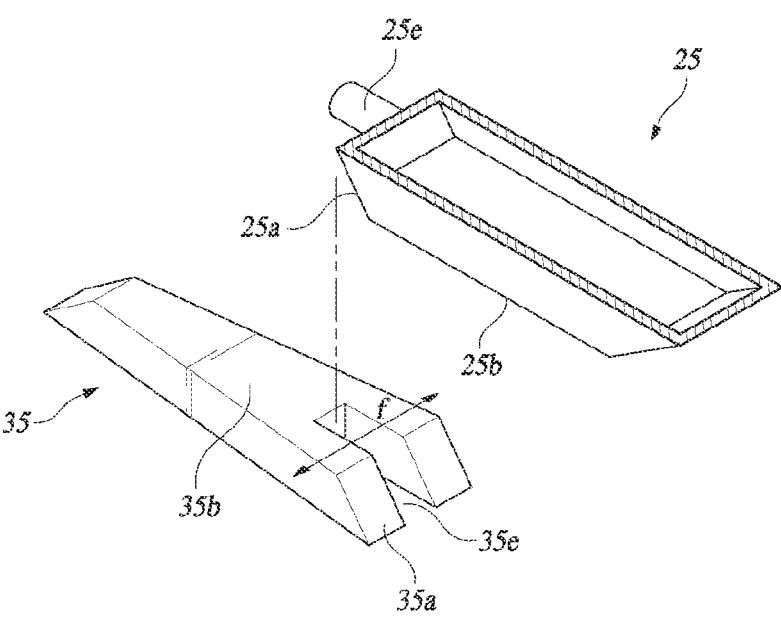
FIGS. 6 and 7 are views illustrating modified examples of an upper orthodontic block and a lower orthodontic block applicable to the orthodontic appliance according to one embodiment of the present invention.
Figure 7:
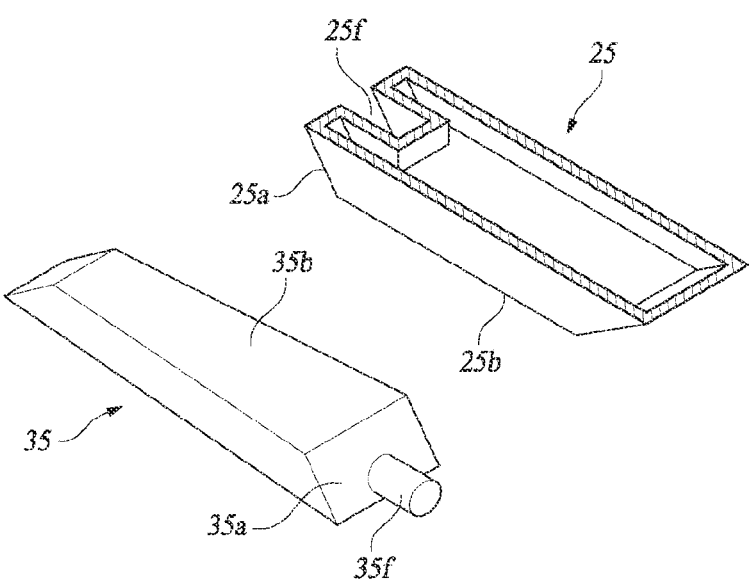

FIGS. 6 and 7 are views illustrating modified examples of the upper orthodontic block 25 and the lower orthodontic block 35 applicable to the orthodontic appliance 10 according to one embodiment of the present invention. Although the upper orthodontic block 25 is integrated with the upper teeth aligner 23 and the lower orthodontic block 35 is integrated with the lower teeth aligner 33, the upper and lower orthodontic blocks 25 and 35 are illustrated as being extracted separately, for convenience of explanation.

Referring to FIG. 6, a protrusion 25e is formed at the center of the pressing inclined plane part 25a of the upper orthodontic block 25. The protrusion 25e is provided as a round bar having a designated diameter, and extends in the horizontal direction in the state in which the protrusion 25e is integrated with the pressing inclined plane part 25a. The horizontal direction indicates a direction parallel to a virtual plane including the contact plane part.

Further, a locking groove 35e is provided in the lower orthodontic block 35. The locking groove 35e is formed in the center of the pushed inclined plane part 35 a, and corresponds to the protrusion 25e. In the state in which the upper and lower teeth aligners 23 and 33 are in contact, the protrusion 25e is inserted into the locking groove 35e, and is thus supported thereby. The upper orthodontic block 25 is not shaken left and right, i.e., in the direction of an arrow f. Application of the protrusion 25e and the locking groove 35e may realize more accurate and effective orthopedic treatment.

Further, in the upper and lower orthodontic blocks 25 and 35 shown in FIG. 7, a locking groove 25f is formed in the upper orthodontic block 25, and a protrusion 35f is formed on the lower orthodontic block 35. The functions of the locking groove 25f provided above and the protrusion 35f provided below are the same as those in FIG. 6.

Figure 8:
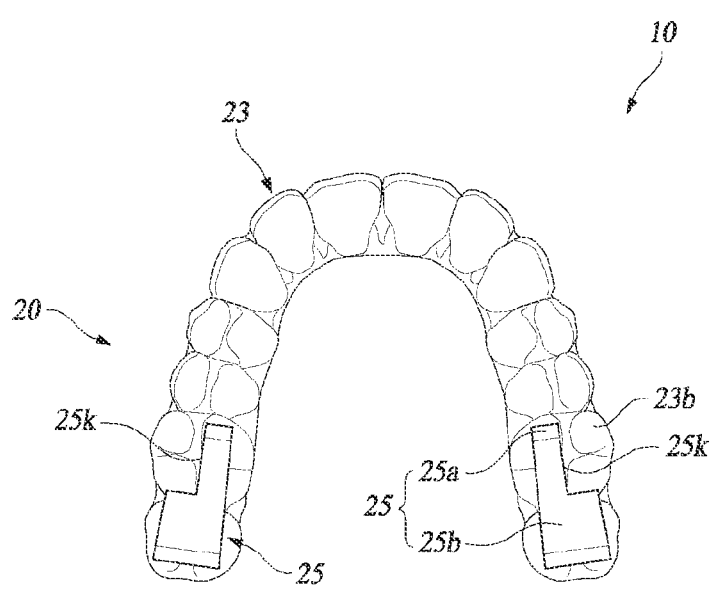
FIG. 8 is a view illustrating another modified example of the upper orthodontic block and the lower orthodontic block according to one embodiment of the present invention.
Figure 8:
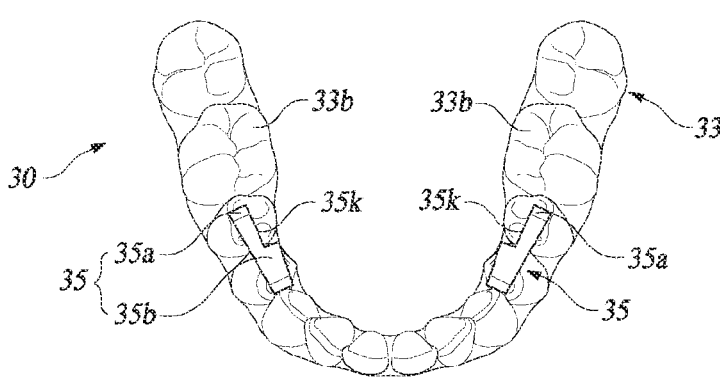

FIG. 8 is a view illustrating another modified example of the upper orthodontic block and the lower orthodontic block according to one embodiment of the present invention.

As shown in this figure, locking grooves 25k and 35k are respectively formed in the outer side parts of the upper orthodontic blocks 25 and the inner side parts of the lower orthodontic blocks 35. The locking grooves 25k and 35k are mutually fitted into each other in the state in which the upper teeth aligner 23 and the lower teeth aligner 33 are in contact. That is, the locking groove 25k of the upper teeth aligner 25 receives a part of the lower orthodontic block, and the locking groove 35k of the lower orthodontic block 35 receives a part of the upper orthodontic block. Such fitting combination may prevent relative lateral movement of the upper and lower orthodontic blocks, in the state in which the upper and lower teeth aligners are in contact.

The upper and lower orthodontic blocks of this type may be effective for a patient having bruxism and clenching due to severe lateral motion of a mandible. Of course, in the case in which a patient has no symptoms of bruxism or it is necessary to allow a patent to freely move a mandible laterally, the locking grooves may be omitted, as shown in FIGS. 1 and 2.

Figure 9:
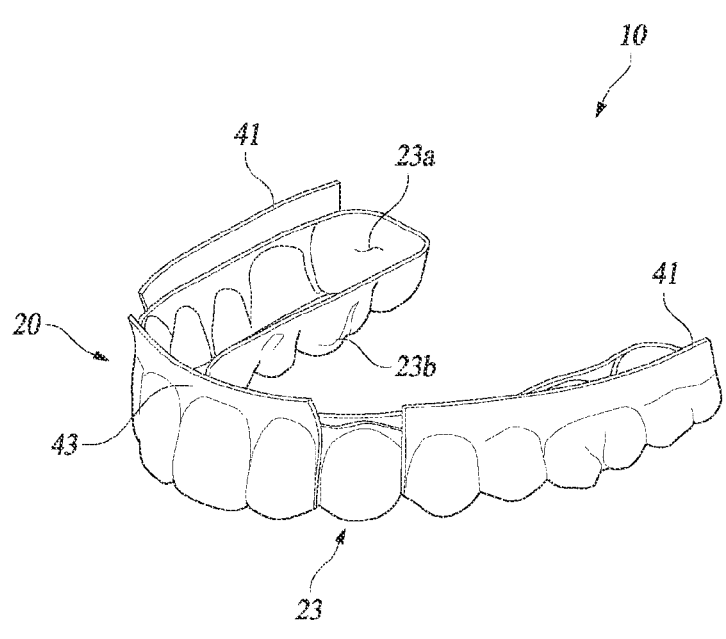
FIG. 9 is a perspective view showing another modified example of the orthodontic appliance according to one embodiment of the present invention.
Figure 9:
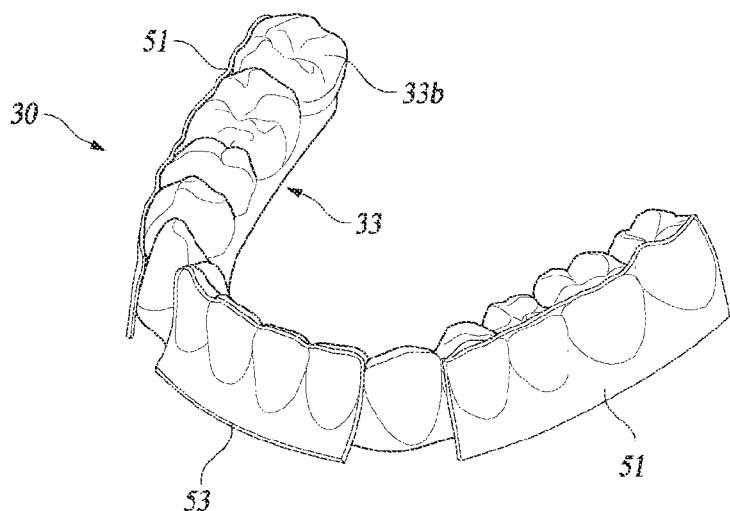

FIG. 9 is a perspective view showing another modified example of the orthodontic appliance 10 according to one embodiment of the present invention.

The orthodontic appliance 10 of this type shown in FIG. 9 has, particularly, a function of laterally expanding arches. That is, in order to expand the maxilla and the mandible in the labial direction and in both sideward directions, upper and lower anterior teeth covers 43 and 53 and upper and lower posterior teeth covers 41 and 51 are applied. The reason why the maxilla and the mandible are expanded is to provide orthopedic treatment.

Although FIG. 9 illustrates that both the anterior teeth cover and the posterior teeth covers are applied to the upper teeth mounting unit 20 and the lower teeth mounting unit 30, whether or not the anterior teeth cover and the posterior teeth covers are applied may be determined by the oral structure of a user (a target person of orthopedic treatment) or the degree of asymmetry thereof.

For example, the upper posterior teeth covers 41 and the upper anterior teeth cover 43 may be applied to the upper teeth aligner 23 but the lower posterior teeth covers 51 and the lower anterior teeth cover 53 may not be applied to the lower teeth aligner 33, or, in contrast, the lower posterior teeth covers 51 and the lower anterior teeth cover 53 may be applied to the lower teeth aligner 33 but the upper posterior teeth covers 41 and the upper anterior teeth cover 43 may be omitted from the upper teeth aligner 23. Further, both the upper posterior teeth covers 41 and the upper anterior teeth cover 43 may be applied to the upper and lower teeth aligners 23 and 33, or the upper posterior teeth covers 41 and the upper anterior teeth cover 43 may be selectively applied to the upper and lower teeth aligners 23 and 33.

The upper teeth mounting unit 20 and the lower teeth mounting unit 30 having the above configuration are manufactured using a vacuum forming machine or a 3D printer, and the entireties of the upper teeth mounting unit 20 and the lower teeth mounting unit 30 are transparent.

The upper posterior teeth covers 41 are integrated with the outer surfaces of the left and right sides of the upper teeth aligner 23, and cover gums supporting molar teeth and premolar teeth. That is, the upper posterior teeth covers isolate the gums from surrounding muscles (cheek muscles) so as to block pressure applied to the gums or the teeth by the muscles. The reason why the pressure applied by the muscles is blocked is to prevent interference of the muscles so as to cause a maxillary arch to expand and grow.

The upper anterior teeth cover 43 is fixed to the front surface of the upper teeth aligner 23, and isolates gums supporting anterior teeth from lip muscles. The upper anterior teeth cover 43 serves to cause the maxilla to grow forwards. For reference, the upper anterior teeth cover 43 is used in treatment of skeletal Class III, and the lower anterior teeth cover 53, which will be described below, is used in correction of skeletal Class II.

The lower posterior teeth covers 51 are integrated with the outer surfaces of the left and right sides of the lower teeth aligner 33, and isolate gums from the cheek muscles. The lower posterior teeth covers 51 are used to prevent interference of the muscles so as to cause a mandibular arch to expand and grow.

The lower anterior teeth cover 53 is provided on the outer surface of the front part of the lower teeth aligner 33, and isolates anterior teeth from the lip muscles. The lower anterior teeth cover 53 may cause forward growth of the mandible.

The upper and lower posterior teeth covers 41 and 51 serve to prevent interference of the surrounding muscles so as to cause normal growth of the maxillary and mandibular arches through expansion thereof, and enable various movements of the teeth as needed. In the same manner, the upper and lower anterior teeth covers 43 and 53 block the influence of the muscles, and simultaneously, cause teeth correction through improvement in permanent teeth eruption paths and teeth movement.

Figure 10:
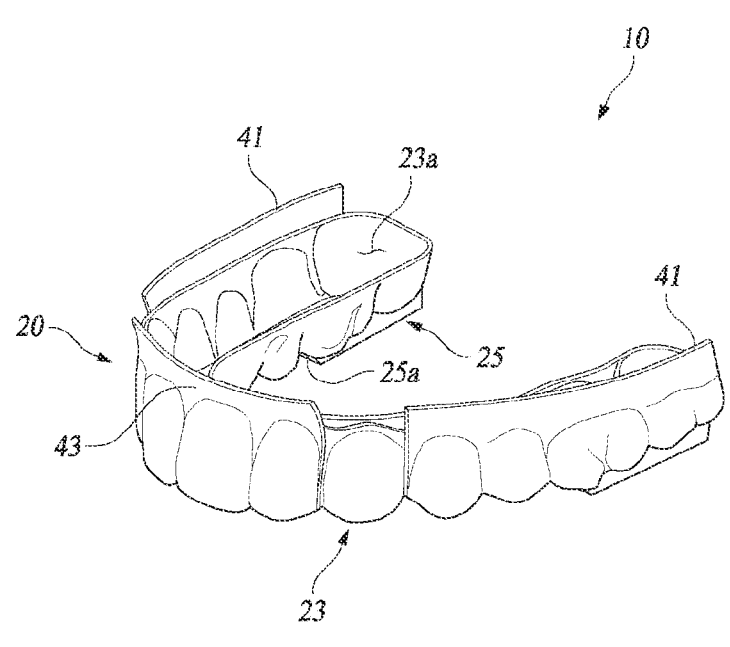
FIG. 10 is a perspective view showing yet another modified example of the orthodontic appliance according to one embodiment of the present invention.
Figure 10:
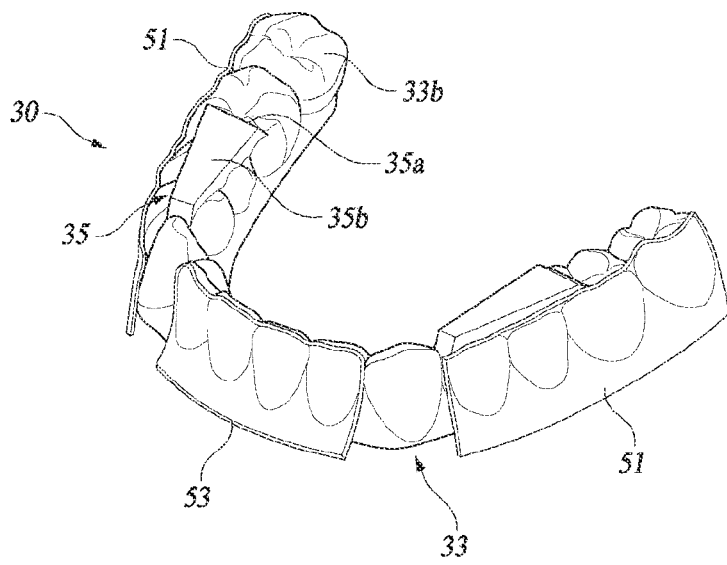

FIG. 10 is a perspective view showing yet another modified example of the orthodontic appliance 10 according to one embodiment of the present invention.

The upper teeth mounting unit 20 of the orthodontic appliance 10 of this type shown in FIG. 10 includes an upper teeth aligner 23, upper orthodontic blocks 25, upper posterior teeth covers 41, and an upper anterior teeth cover 43. Further, the lower teeth mounting unit 30 includes a lower teeth aligner 33, lower orthodontic blocks 35, lower posterior teeth covers 51, and a lower anterior teeth cover 53. A description of the elements forming the upper teeth mounting unit 20 and the lower teeth mounting unit 30 is the same as stated above.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An orthodontic appliance with an orthopedic function comprising:

an upper teeth aligner configured to be mounted on a user's upper teeth to correct arrangement of the user's upper teeth;

a lower teeth aligner configured to be mounted on the user's lower teeth to correct arrangement of the user's lower teeth; and occlusal force conversion units respectively provided on the upper teeth aligner and the lower teeth aligner, and configured to interact with each other in a state in which the upper and lower teeth aligners are in contact, so as to cause a relative position of a mandible with respect to a maxilla to move to a normal position, wherein the occlusal force conversion units comprise upper orthodontic blocks located on some parts of a bottom surface of the upper teeth aligner and configured to protrude downwards, each of the upper orthodontic blocks comprising a pressing inclined plane part; and lower orthodontic blocks located on some parts of an upper surface of the lower teeth aligner and configured to protrude upwards, each of the lower orthodontic blocks comprising a pushed inclined plane part pushed by a pressure applied by the pressing inclined plane part, wherein the pressing inclined plane part is lowered while sliding along the pushed inclined plane part to apply the pressure to the pushed inclined plane part at a time of occlusion, wherein:

a protrusion configured to extend horizontally from the pushed inclined plane part of each of the lower orthodontic blocks is formed on the pushed inclined plane part, the protrusion being an elongated part extended from the pushed inclined plane part; and a locking groove configured to receive the protrusion, by holding the protrusion between two opposing inner surfaces of the locking groove, in the state in which the upper and lower teeth aligners are in contact, is formed in the pressed inclined surface part of each of the upper orthodontic blocks, the locking groove being opened to a lower surface of each of the upper orthodontic blocks.

2. The orthodontic appliance according to claim 1, further comprising:

upper covers located on an outer surface of the upper teeth aligner, and configured to isolate gums from muscles configured to surround the gums and thus to block pressure of the muscles applied to the gums so as to cause growth of a maxillary arch.

3. The orthodontic appliance according to claim 2, further comprising:

lower covers located on an outer surface of the lower teeth aligner, and configured to isolate gums from muscles configured to surround the gums and thus to block the pressure of the muscles applied to the gums so as to cause growth of a mandibular arch.

4. The orthodontic appliance according to claim 3, wherein the lower covers comprise:

a lower anterior teeth cover fixed to a front surface of the lower teeth aligner so as to isolate the gums from lip muscles.

5. The orthodontic appliance according to claim 3, wherein the lower covers comprise:

lower posterior teeth covers fixed to both side parts of the lower teeth aligner so as to isolate the gums from cheek muscles.

6. The orthodontic appliance according to claim 2, wherein the upper covers comprise:

an upper anterior teeth cover fixed to a front surface of the upper teeth aligner so as to isolate the gums from lip muscles.

7. The orthodontic appliance according to claim 2, wherein the upper covers comprise:

upper posterior teeth covers fixed to both side parts of the upper teeth aligner so as to isolate the gums from cheek muscles.

* * * * *